US011395636B2

(12) United States Patent
Meyer (10) Patent No.: US 11,395,636 B2
(45) Date of Patent: Jul. 26, 2022

(54) PATIENT SUPPORT FACILITY AND MEDICAL IMAGING FACILITY

(71) Applicant: Siemens Healthcare GmbH, Erlangen (DE)

(72) Inventor: Michael Meyer, Hausen (DE)

(73) Assignee: Siemens Healthcare GmbH, Erlangen (DE)

( * ) Notice: Subject to any disclaimer, the term of this patent is extended or adjusted under 35 U.S.C. 154(b) by 206 days.

(21) Appl. No.: 16/819,563

(22) Filed: Mar. 16, 2020

(65) Prior Publication Data

US 2020/0297291 A1 Sep. 24, 2020

(30) Foreign Application Priority Data

Mar. 21, 2019 (DE) .......................... 102019203882.4

(51) Int. Cl.
*A61B 6/04* (2006.01)
*A61G 7/05* (2006.01)
*A61B 6/00* (2006.01)
*A61G 7/08* (2006.01)
*A61G 13/04* (2006.01)
*A61G 13/06* (2006.01)

(52) U.S. Cl.
CPC .............. *A61B 6/04* (2013.01); *A61B 6/4405* (2013.01); *A61B 6/54* (2013.01); *A61G 7/0528* (2016.11); *A61G 7/08* (2013.01); *A61G 13/04* (2013.01); *A61G 13/06* (2013.01); *A61G 2203/12* (2013.01); *A61G 2203/22* (2013.01)

(58) Field of Classification Search
CPC ........... A61B 6/04; A61B 6/4405; A61B 6/54; A61G 7/0528; A61G 7/08; A61G 13/00; A61G 13/04; A61G 13/06
See application file for complete search history.

(56) References Cited

U.S. PATENT DOCUMENTS

| 2011/0154569 | A1 | 6/2011 | Wiggers | |
|---|---|---|---|---|
| 2013/0000438 | A1* | 1/2013 | Ouellet | ................ B25J 17/0275 |
| | | | | 74/490.03 |
| 2013/0292918 | A1 | 11/2013 | Schlee | |
| 2013/0326812 | A1* | 12/2013 | Jackson | ............. A61G 13/0036 |
| | | | | 5/607 |
| 2017/0196748 | A1 | 7/2017 | Gaiser | |
| 2019/0343701 | A1 | 11/2019 | Dirauf | |
| 2020/0016927 | A1 | 1/2020 | Dietrich | |

FOREIGN PATENT DOCUMENTS

| CN | 201558247 U | 8/2010 |
|---|---|---|
| DE | 102014115901 A1 | 5/2016 |
| DE | 102018211669 A1 | 8/2019 |
| WO | WO2018130315 A1 | 7/2018 |

OTHER PUBLICATIONS

German Office Action for German Application No. 10 2019 203 882.4 dated Feb. 6, 2020.

* cited by examiner

*Primary Examiner* — Fredrick C Conley
(74) *Attorney, Agent, or Firm* — Lempia Summerfield Katz LLC (57) ABSTRACT

A patient support facility including at least one patient support plate and at least two supports for the patient support plate. Each of the supports are configured to be mobile has an autonomous drive module with a chassis permitting movements and rotations in all horizontal directions, a drive facility, and a control unit. The patient support facility includes a control facility that is configured to operate the drive modules in a coordinated and individual manner.

19 Claims, 6 Drawing Sheets

PATIENT SUPPORT FACILITY AND MEDICAL IMAGING FACILITY

CROSS REFERENCE TO RELATED APPLICATIONS

This application claims the benefit of DE 102019203882.4 filed on Mar. 21, 2019, which is hereby incorporated by reference in its entirety FIELD Embodiments relate to a patient support facility including at least one patient support plate and at least two supports for the patient support plate.

BACKGROUND

Patient support facilities are used in the medical environment for a plurality of procedures, examples of which, in addition to imaging tasks for which the patient must be positioned lying down, also include examination and/or treatment tasks, for example surgical interventions. For the medical tasks, different kinds of patient support facilities have been developed, for example patient support facilities for imaging facilities that dispense as far as possible with components that interfere with the imaging, for example patient support facilities with carbon fiber plates for X-ray facilities, and patient support facilities that may also be described as operating tables for medical surgical interventions, for example such in which several partial plates of the patient support plate are pivotable against one another, for example by a pivot facility. Different patient support facilities are available for different applications, such as radiography tables, angiography tables, computed tomography tables, operating tables, etc.

In the case of application sequences, the highly specialized solutions necessitate a frequent repositioning of patients and a high level of effort and cost.

BRIEF SUMMARY AND DESCRIPTION

The scope of the present disclosure is defined solely by the appended claims and is not affected to any degree by the statements within this summary. The present embodiments may obviate one or more of the drawbacks or limitations in the related art.

Embodiments provide a patient support facility that may be used flexibly and operated easily.

In an embodiment, a patient support facility is provided that is mobile, includes an autonomous drive module with a chassis permitting movements and rotations in all horizontal directions, a drive facility, and a control unit. The patient support facility includes a control facility that is configured to operate the drive modules in a coordinated and individual manner.

In an embodiment, a patient table system with a modular structure is provided with which patients may be placed in a wide variety of positions. Embodiments provide that the patient support facility also includes several exchangeable patient support plates, including at least one imaging plate made, for example, from carbon fiber and including a one-piece positioning surface and at least one operating plate including at least two partial plates that are movable, for example pivotable, against one another. Frequent use is made of the singular in the following description, wherein reference is then made for example, to that patient support plate that is arranged on at least two of the at least two supports.

Embodiments provide a modular patient support system including at least two supports for at least one or at least two patient support plates. The supports may also be described as support facilities or a "table base". The at least one patient support plate may be an imaging plate made from carbon fiber and including a one-piece positioning surface and/or a patient support plate, for example, an operating plate, including several partial plates with articulated joints, in which for example the middle partial plate may be made from metal and only the outer partial plates from carbon fiber. Other patient support plates are possible.

The supports may include an autonomous drive module with a chassis permitting movements and rotations in all horizontal directions, a drive facility, and a control unit. Autonomous drive modules are also known as ADMs. Robotic chassis including rollers on each wheel may include rollers that are slanted by 45° against the circumferential direction so as to provide a movement in any direction (omnidirectional drive module). Autonomous drive modules may also be used for the autonomous movement of the supports, for example toward a target position that may be defined in relative or absolute terms, and permit an extremely high level of flexibility with regard to the patient support facility. The control unit or at least the control facility is configured to move the support in at least a partially automated manner into a target posture by actuating the drive facility. The term posture is understood here, as is customary, to refer to the position and orientation.

To provide an autonomous operation of the drive module, the drive module may further include at least one position determination device configured for determining a current posture (position and orientation) of the support. The posture may be determined in relative terms (relative to other supports and/or other devices/components) and/or in absolute terms. For autonomous operation, in addition to the position determination, the drive module may include further sensor technology such as distance sensors and/or imaging sensors. Other types of sensors, such as those associated with a magnetic guidance system, may also be used. For example, when a target posture is specified to the control unit of a drive module and/or when a target trajectory is specified for the drive module, the control unit of the drive module may control the autonomous operation of the support to the target posture, for example by specific trajectory planning. The control unit communicates directly and/or indirectly via the control facility or further components of the control facility communicate with the control unit of a drive module of another support, to which the patient support plate is also attached, in order to provide coordination when attached to the same patient support plate. It is also possible for the coordination to be provided by a higher-level control unit of the control facility. Specific possibilities/algorithms for the autonomous operation of ground-operated mobile objects are already known.

Because the drive modules of the supports may be operated both individually and in a coordinated manner, using, for example, the same drive instructions, significantly increases the application possibilities and the operating convenience with respect to the patient support facility. Embodiments provide for a patient support plate attached to two supports that, through the coordinated operation of both drive modules, the patient couch thus formed and with it, where appropriate, the patient positioned thereon may be moved within a room or even between different rooms. A coordinated operation of the drive modules in the same manner makes it possible for example to move the supports with the patient support plate arranged thereon into a target position. A coordination of the drive modules requiring a different actuation is provided for example if a particular target orientation is to be assumed that differs from the current orientation of the patient couch thus formed. At the same time, however, embodiments also provide drive modules to be actuated individually, for example if a support is to remain in its position and the other support is to be moved into a different position below the patient support plate. This may be useful for example if a particular region of the patient support plate and thus of the patient is to be supported effectively or if certain regions are to be set without supports for imaging purposes. The other support (if the patient support plate includes two supports) may then remain in its position or at a later time also be brought into a different position below the patient support plate. The supports may be configured in such a way that, even if arranged only on one side of the patient support plate, the supports are still capable of supporting the same, where appropriate including the patient positioned thereon, without tilting. The supports may include at least one mass element to provide a center of gravity lying in the support region up to at least a predetermined weight of a patient. The configuration of the mass element may also take into consideration a case in which the patient support plate is to be supported in all cases by (at least) two supports.

Robotic, autonomous drive modules are linked together to cooperate in order to realize an adjusted, flexible patient support. The described patient support facility is equally usable for different imaging modalities, as a patient transfer system and as an operating table. The current complexity in the area of patient support may be significantly reduced.

The control facility may include at least one of the control units and/or be formed by at least one of the control units. The control units of the drive modules may form at least one part of the control facility, to which end the control units may communicate wirelessly with one another and/or with a portion of the control facility external to the support via a communication link and/or a communication network. For example, one of the drive modules may be configured as a type of "master" and coordinate the overall operation of the control units of the drive modules, or also actuate its own drive module or other drive modules individually. If the patient support facility is to be used in conjunction with at least one imaging facility, it is also possible for control units of the corresponding medical imaging facility to be integrated into the control facility and to form the same in part or in whole, so that a coordination with components of the medical imaging facility may then also take place. An external control facility or an external portion of the control facility may also be realized as part of an operator control of the patient support facility. Such an operator control, that may be provided as a mobile or handheld operating device, may be realized, for example, by a smartphone and/or a tablet, that includes suitable possibilities for communicating with the control units of the drive modules and on which a software application (app) may run in order to realize the actuation. The operator control may include a visualization facility, for example, a display, that improves the manual or semi-manual control. The operator control may include a position determination device for determining a current position or orientation of the operator control so that, for example, a current position or even posture of the operator control may be used as the target position or target posture for the patient support facility. Then, for example, an operator with the operator control, e.g. mobile, handheld operating device, may proceed to a location to which a patient couch formed, for example, from two supports and one patient support plate is to be moved and "summon" it to the location.

The patient support plate may include a first guidance facility, for example a rail, and the supports may include a second guidance facility, for example a corresponding rail or receptacle. The first and a respective second guidance facility are configured to engage with one another in order to arrange the patient support plate in a detachable manner on at least one of the supports. It is therefore possible for example to use a rail system that runs in the longitudinal direction of the patient support plate to connect the patient support plate reversibly to the support. If, for example, a dovetail-type is provided, the patient support plate may be pushed onto the supports. The advantage of such a rail system or of a guidance system is that at least one degree of freedom of movement remains available in one direction, for example, in the longitudinal direction of the patient support plate, providing, for example, supports to be pushed against the patient support plate below the same in the longitudinal direction through operation of the drive facility of the drive modules.

The supports may include at least one height adjustment facility and/or at least one tilting facility for tilting a patient support plate arranged on the respective support from the horizontal. On account of the height adjustment facilities of all supports supporting the patient support plate being operated in the same way, it is thus possible, for example, to set a desired height of the patient support plate. However, many positions of a patient are also known, for example, during surgical interventions and/or other treatments, in which the patient is to be positioned tilted relative to the horizontal. At least one tilting facility may be provided that is configured to tilt the patient support plate about at least a horizontally running axis from the horizontal. The height adjustment and/or tilting facilities are already known. For example, height adjustment facilities may be implemented as pneumatic and/or electrical lifting columns, while tilting facilities may include a suitable pivot mounting or rocker joints. The tilting facility may be implemented passively, for example as a passive pivot mounting of the patient support plate, since a tilting about an axis perpendicular to the longitudinal direction of the patient support plate may already be provided, for example by different height settings of the height adjustment facilities of different supports supporting the patient support plate. At least two height adjustment facilities of different supports together may also form at least one part of a tilting facility.

Each support may include two height adjustment facilities that together implement a tilting facility disposed in a transverse direction perpendicular to the longitudinal direction of the patient support plate. A tilting about the longitudinal axis of the patient support plate by height adjustment facilities is also possible, for example, by providing several height adjustment facilities on one support, that follow one another in the transverse direction, for example combined in turn with a suitable pivot mounting of the patient support plate on the support. The position of the patient support plate tilted about the longitudinal axis of the patient support plate may also be described as a canted position. Equipping the supports with two height adjustment facilities provides both a height adjustment and a tilting and canting.

Where a tilting of the patient support plate on the supports is provided the patient support plate may include at least one fastening/fixing device for fastening at least one part of the patient on the patient support plate. The patient does not slide down from the patient support plate.

Where height adjustment facilities and/or tilting facilities are provided, the height adjustment facility may include at least one controllable actuator and/or the tilting facility including at least one controllable actuator of each support that are controllable by the control facility. The height adjustment facilities and/or tilting facilities are also incorporated into the overall operation, so that, for example, certain relative and/or absolute target postures of the supports may also be associated with corresponding settings of the height adjustment facility and/or the tilting facilities in order to provide further control coordination. In all cases, the controllability via the same control facility provides a shared, central control concept. For example, an operator control such as a mobile, handheld operating device may thus also be configured to operate the height adjustment facilities and/or tilting facilities.

The control facility may be configured to autonomously produce different relative and/or absolute target postures of the supports that are configured for actuating at least the drive modules is configured to produce settings of a setting data record describing settings that contain an at least relative posture of the supports and/or to autonomously assume an absolute target position and/or an absolute target position range of a target data record. Setting data records and/or target data records may be specified manually, for example by an operator control. Frequently required relative or absolute target postures may be stored as settings, such that they may be retrieved.

Embodiments provide where the control facility includes a storage device or is configured to access a storage device. A database with several setting data records and/or target data records that may be selected automatically and/or by the user is stored in the storage device. The database or the storage device may therefore form a part of the control facility, but may also be stored for example externally in an accessible manner, for example on a server of a network and/or the Internet. Target positions or target position ranges may also be extended as target postures or target posture ranges.

At least one setting data record may also include at least one item of setting information for the height adjustment facility and/or the tilting facility. Stored or predefined settings may also refer to the height and/or the tilting state of the patient support plate.

A database with setting data records and/or target data records may be predefined at least partially, for example, already at the time of delivery, and containing for example standards or basic settings relating to the relative target position or target posture that are frequently required and may for example be selected accordingly by the user, for example, by an operator control, but also automatically, for example as a function of information about an impending examination and/or treatment of a patient that may already be present in an information system such as a hospital information system and/or a radiology information system to which the control facility includes access. Setting data records and/or target data records may however also be created by an operator and for example stored in the database if the setting data records have proven useful or are required more frequently. User profiles may be created so that different users may create and save the setting data records and/or target data records the users require in each case. The operator control, for example the mobile, handheld operating device, also includes a control element via which a current setting may be stored as a setting data record and/or a current position and/or posture may be stored as a target data record.

An embodiment provides an imaging facility including a patient support facility and a recording arrangement supported on a support facility. The control facility is configured to consider a current posture of the recording arrangement relative to the supports during actuation of the drive modules.

The current settings relating to the recording arrangement may be used, in an X-ray facility including for example an X-ray tube assembly and an X-ray detector, for example the posture thereof, for example in order to bring certain regions of the patient support plate and thus of a patient supported thereon into the imaging range. The imaging facility may be an X-ray facility, in which the support facility is configured with a mobile C-arm. An X-ray tube assembly and an X-ray detector are arranged opposite one another on the C-arm. The patient support facility may also be used for other imaging modalities, such as magnetic resonance imaging and/or computed tomography.

The support facility, for example the mobile C-arm, may include a further, autonomous drive module with a chassis permitting movements and rotations in all horizontal directions, that may be actuated by the control facility in a coordinated manner with the drive modules of the supports and/or independently thereof. At least one further drive module of the imaging facility may also be included in the control facility, so that it is also possible to operate the further drive module in a coordinated manner with the drive modules of the supports of the patient support facility. Independent operation may of course also be used, for example if the support facility is to be moved away from the patient support facility automatically to provide better access.

DETAILED DESCRIPTION

Figure 1:
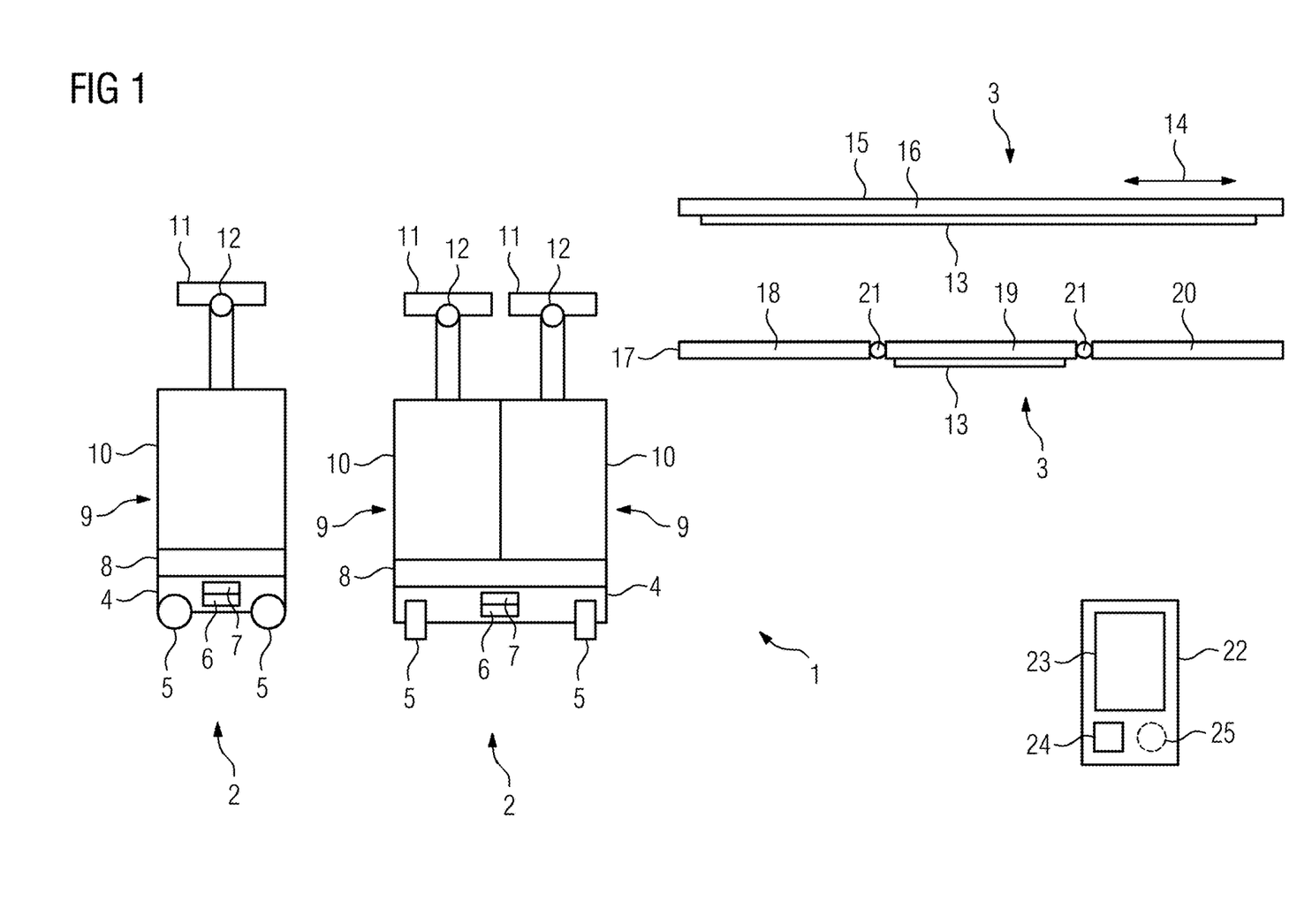
FIG. 1 depicts a patient support facility according to an embodiment in a disassembled state.

FIG. 1 depicts a schematic diagram of components of a patient support facility 1 according to an embodiment. FIG.

1 includes two supports 2. The supports 2 are shown from different directions, although they may be configured in an identical manner. The patient support facility 1 further includes two patient support plates 3.

The supports 2, that may also be described as mobile columns, initially each have one autonomous drive module 4 with four wheels 5 in each case, that are part of a chassis permitting movements and rotations in all horizontal directions, a drive facility 6 and a control unit 7, that are described in more detail in the following.

In this embodiment, the supports 2 further include an optional mass element 8 adjacent to the drive module 4, that provides that the center of gravity of a patient couch formed from two supports 2 and a patient support plate 3 is maintained in the support region up to a certain patient weight, therefore preventing tilting even in the event of an extremely lateral arrangement of the supports 2.

Each support 2 further includes height adjustment facilities 9, each including two lifting columns 10 adjacent to one another in the transverse direction, that may be operated electrically and/or pneumatically. One support section, that is formed by a second guidance facility 11, is connected to the lift columns 10 by way of a pivot mounting 12 associated with a tilting facility.

In this context, the patient support plates 3 each include a first guidance facility 13, that may engage with the second guidance facilities 11 such that the patient support plates 3 may be arranged in the longitudinal direction 14 of the patient support plates 3 so as to be relatively displaceable onto the supports 2. The first and second guidance facilities 13, 11 are each configured as rails, that are shaped accordingly such that they may engage with each other. A dovetail-type configuration may be used, for example.

The first of the two patient support plates 3, depicted in the upper part of FIG. 1, is configured as an imaging plate 15, that includes a carbon-fiber plate 16 forming a one-piece, continuous positioning surface, that interferes with or influences various imaging modalities to the least possible extent.

The second patient support plate 3, depicted in the lower part of FIG. 1, is an operating plate 17 including three partial plates 18, 19, 20, that are mounted tiltably with respect to one another via pivot facilities 21. The middle partial plate 19 may be produced from metal, for example steel, and includes the first guidance facility 13. The partial plates 18, 20 may be produced from carbon fiber in a lightweight construction.

The patient support facility 1 depicted in FIG. 1 further includes an operator control in the form of a mobile, handheld operating device 22, that may be configured for example as a smartphone or a tablet with a corresponding software application (app). The operating device 22 includes a display 23, for example, a touchscreen, and includes at least one control unit 24. The operating device 22 may also contain a storage medium 25 associated with a control facility of the patient support facility 1, configured from the control units 7 and 24, in which storage medium a database including setting data records and target data records is stored, as explained in more detail in the following. The database may also be stored externally in a manner accessible by the control facility, for example on a server of a local network and/or of the Internet.

Both the drive modules 4 and the operating device 22 include a position determination device to be able to determine a current position and orientation, e.g. posture, of the respective component, both in absolute terms and relative to one another. The drive modules 4 and the operating device 22 may also include further sensors, in the case of the drive module 4, for example, such that support autonomous drive operation of the drive modules 4 and thus of the supports 2, as is known in principle.

Figure 2:
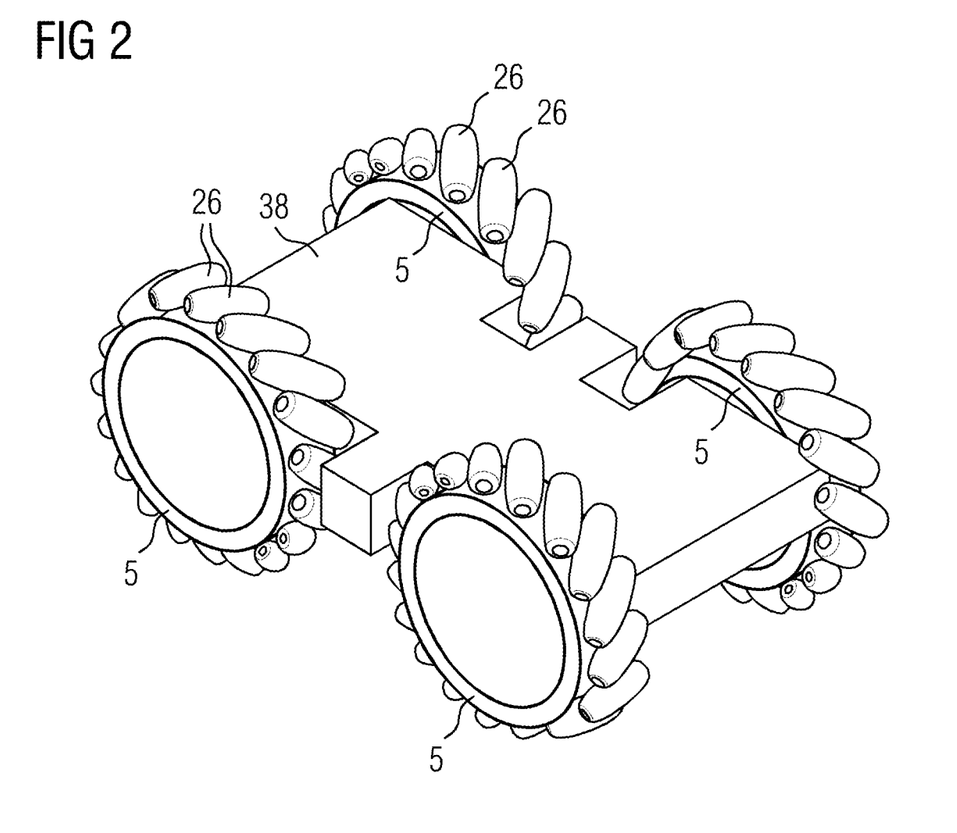
FIG. 2 depicts a schematic diagram of an autonomous drive module according to an embodiment.

FIG. 2 depicts a slightly more detailed schematic diagram of a drive module 4. For the purpose of producing the omnidirectionality, in other words movement and rotation in all horizontal directions, the chassis 27 of the drive module 4 includes four so-called Mecanum wheels 5, the roller elements 26 of which are rotated in each case by 45° (see also for example US 2013/0292918 A1 in this regard).

The control facility of the patient support facility 1 formed from (or at least including) the control units 7 and 24 is configured to actuate the drive modules and the height adjustment facilities/tilting facilities in a coordinated and independent manner. For example, the coordinated operation of the drive modules 4 provides a patient couch formed by arranging one of the patient support plates 3 on the supports 2 to be brought into a target position and/or into a target orientation, for example, a target posture. An autonomous movement of the patient couch may be provided within rooms or even into other rooms. The patient couch may, for example, assume optimum relative or absolute postures for specific examinations and/or treatments. The settings or target positions/target orientations may be specified manually by the operating device 22, but may also be stored in the database, for example, as setting data records including settings and/or target data records containing target positions and/or target orientations. The data records may then be retrieved automatically by the control facility and/or manually by an operator on the display 23. Since both the drive module 4 and the operating device 22 include position determination devices, current posture information identified may be considered at any time in the overall control. Specific examples regarding different settings will be explained in more detail with reference to the following figures. The patient support plates 3 and the supports 2 are shown abstracted compared to FIG. 1 for improved illustration.

Figure 3:
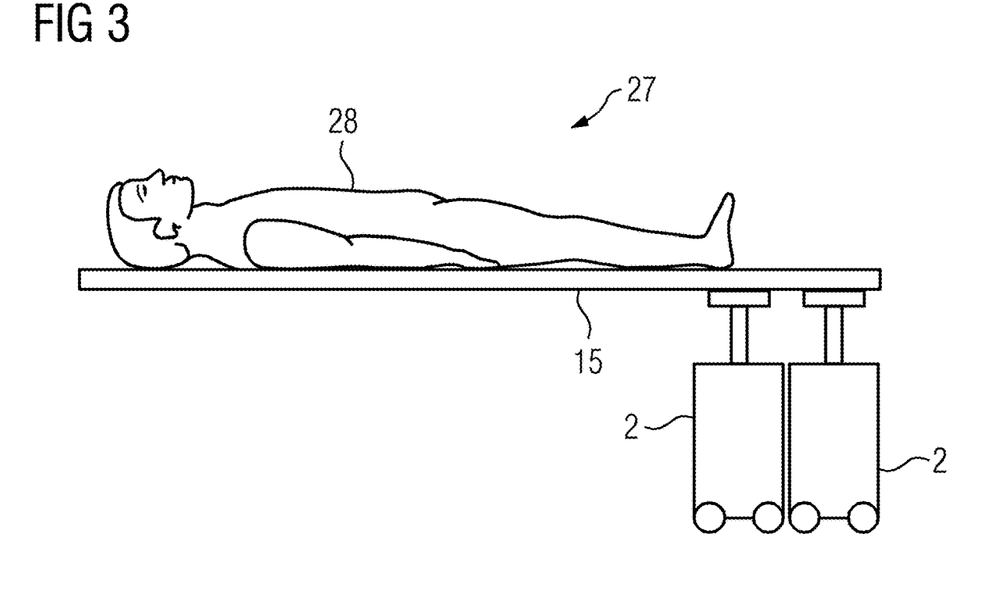
FIG. 3 depicts a first setting of a patient couch formed from the patient support facility according to an embodiment.

In FIG. 3, the first setting of a patient couch 38, that is formed by the imaging plate 15 as a patient support plate 3, is used for an angiographic imaging of the patient 28, for example with an X-ray facility including a C-arm as the imaging facility, since both supports 2 are arranged at one end of the patient support plate 3 and the patient 28 is ultimately supported freely by the carbon-fiber plate 16 so as to neither appreciably obstruct the X-ray radiation nor excessively restrict the freedom of movement of the C-arm around the patient.

Figure 4:
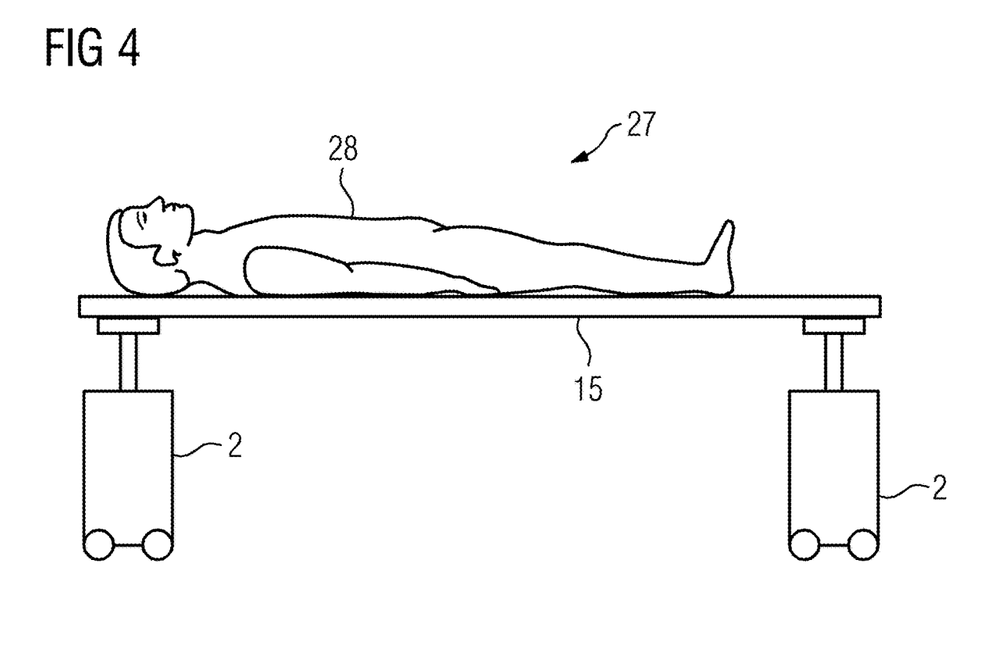
FIG. 4 depicts a second setting of a patient couch formed from the patient support facility according to an embodiment.

FIG. 4 depicts a second setting of the patient couch 38, that may be generated from the setting in FIG. 4 through the autonomous, individual movement, controlled by the control facility, of the left support 2 to the other end of the imaging plate 15. The movement along the longitudinal direction 14 is possible without any problems on account of the embodiment of the guidance facilities 11, 13, as described. The setting depicted in FIG. 4 may be used for radiographic examinations, in which for example the X-ray detector or the X-ray tube assembly may be positioned without any problems in required positions below the patient 28.

Figure 5:
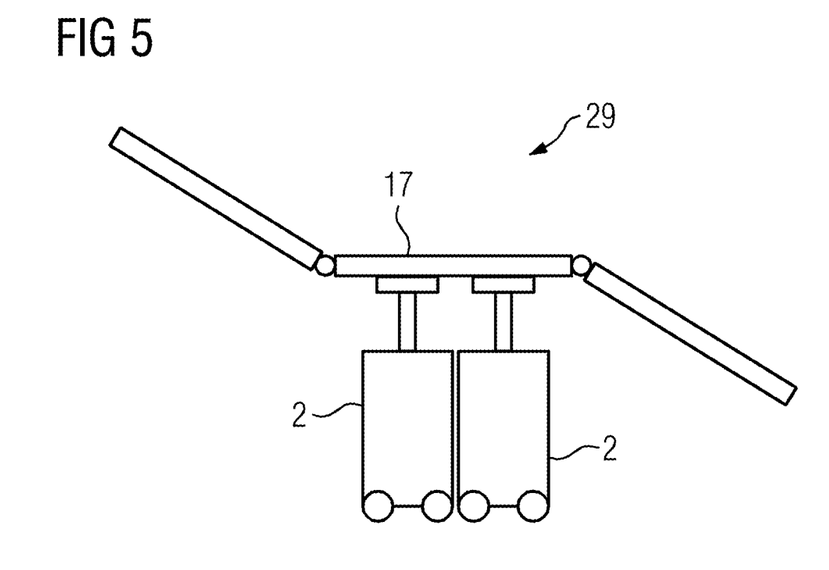
FIG. 5 depicts a third setting of a patient couch formed from the patient support facility according to an embodiment.

FIG. 5 depicts a typical position for an operation where the operating plate 17 includes been used to set up a patient couch 29.

Figure 6:
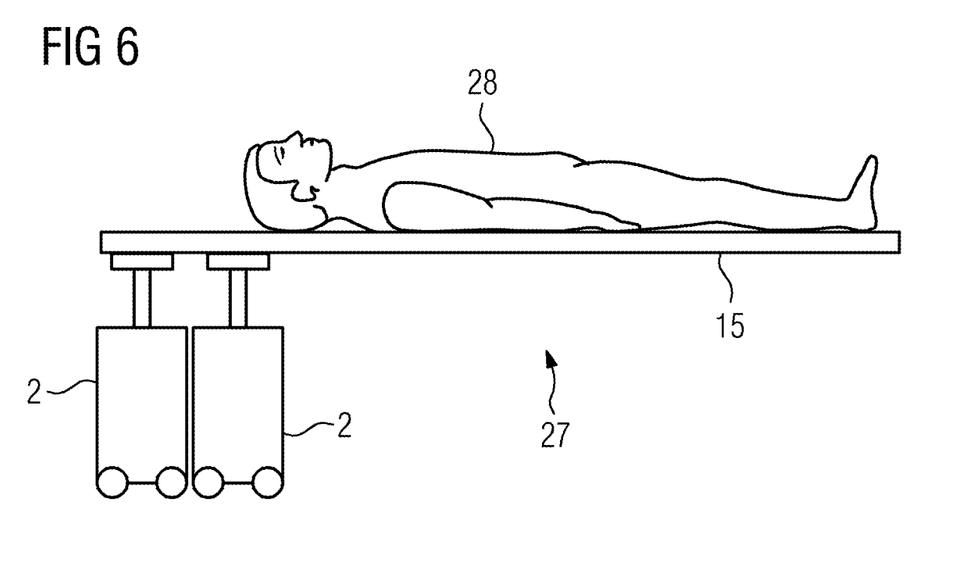
FIG. 6 depicts a fourth setting of a patient couch formed from the patient support facility according to an embodiment.

FIG. 6 depicts a further setting of the patient couch 38, in which a free access to the legs has been created by the right support 2 also being moved to the head end.

Figure 7:
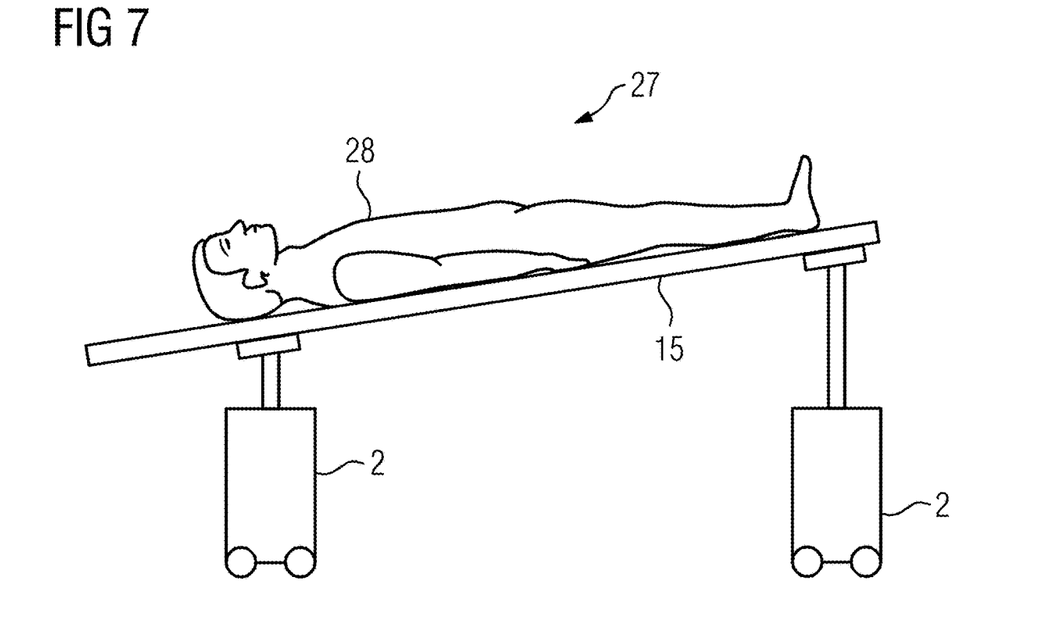
FIG. 7 depicts a fifth setting of a patient couch formed from the patient support facility according to an embodiment.

FIG. 7 depicts a setting of the patient couch 38 that may be used for cardiac treatment, for example cardiac massage, as the imaging plate 15 is set on a slant on account of the different settings of the lift columns 10 of the supports 2, and the left support 2 is located exactly below the heart, where it provides for excellent stabilization. For slanted settings, the patient support plate 3 used in each case may moreover also have a fastening device for the patient (not shown in more detail here).

Figure 8:
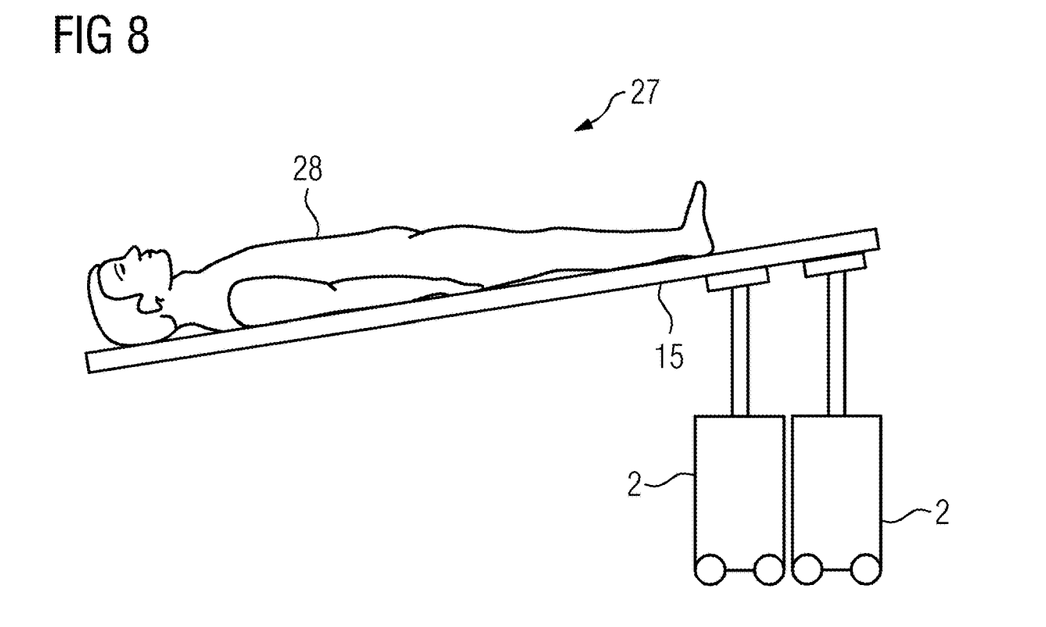
FIG. 8 depicts a sixth setting of a patient couch formed from the patient support facility according to an embodiment.

FIG. 8 depicts a setting of the patient couch 38 in which an even greater tilting is achieved, and the head is thus supported at an even lower level.

Figure 9:
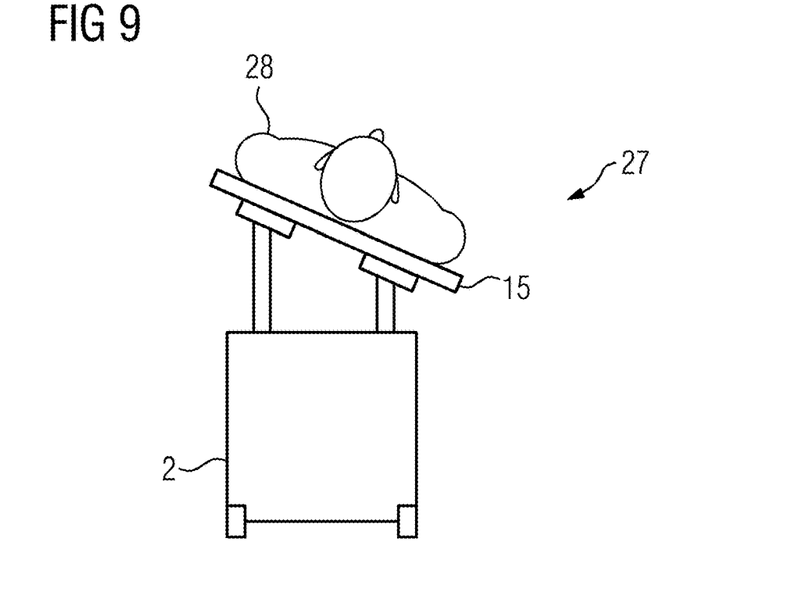
FIG. 9 depicts a seventh setting of a patient couch formed from the patient support facility according to an embodiment.

FIG. 9 depicts that, on account of the two lift columns 10 that follow one another in the transverse direction (see also FIG. 1), a canted position of the patient support plate 3, here in turn by way of example the imaging plate 15, is possible in that different settings of the two height adjustment facilities 9 produce a tilting about the longitudinal direction 14.

Figure 10:
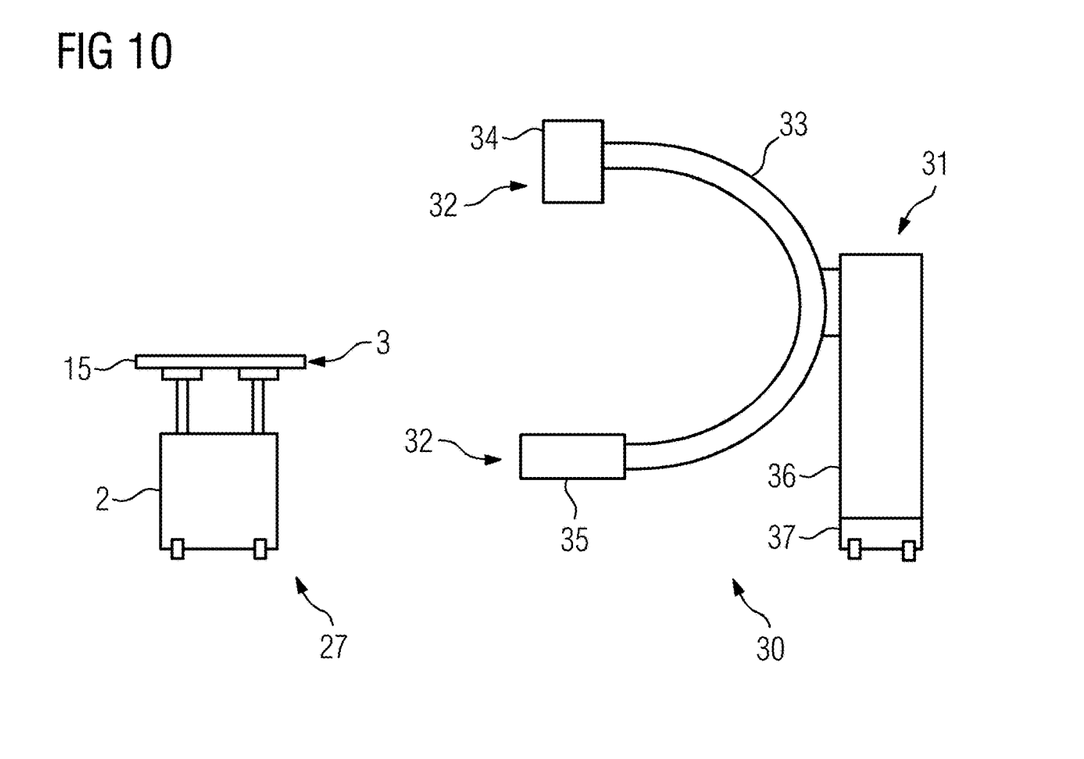
FIG. 10 depicts a medical imaging facility according to an embodiment.

FIG. 10 depicts a schematic diagram of an imaging facility 30 that in addition to the patient support facility 1, represented here by the patient couch 38, also includes an image recording arrangement 32 supported by a support facility 31. The support facility 31 includes a C-arm 33, on which an X-ray tube assembly 34 and an X-ray detector 35 are arranged opposite one another. The C-arm 33 is supported in a movable manner by a stand 36, that is also equipped with a further, autonomous drive module 37, that is configured in the same way as the drive module 4. The drive module 37 and the settings of the recording arrangement 32 may also be taken into consideration accordingly during the control operation of the control facility. The operating device 22 may also be used to operate the imaging portion of the imaging facility 30.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A patient support facility comprising:
   at least one patient support plate;
   at least two supports for the patient support plate, wherein each of the at least two supports are configured to be mobile and each comprise an autonomous drive module including a chassis that is configured to permit movements and rotations in all horizontal directions, a drive facility, and a control unit; and
   a control facility configured to operate the drive modules in a coordinated and individual manner, the control facility further configured to generate settings of a setting data record describing settings that contain an at least relative posture of the supports or is configured to autonomously assume an absolute target position or an absolute target position range of a target data record.

2. The patient support facility of claim 1, wherein the at least one patient support plate comprises a plurality of exchangeable patient support plates comprising at least one imaging plate made from carbon fiber and including a one-piece positioning surface and at least one operating plate comprising at least two partial plates configured to move against one another.

3. The patient support facility of claim 1, wherein the patient support facility further comprises a first guidance facility, wherein the at least two supports include a second guidance facility, wherein the first and a respective second guidance facility are configured to engage with one another in order to arrange the at least one patient support plate in a detachable manner on at least one of the at least two supports.

4. The patient support facility of claim 1, wherein each of the at least two supports includes at least one height adjustment facility, at least one tilting facility for tilting the at least one patient support plate, or at least one height adjustment facility and at least one tilting facility for tilting the ate least one patient support plate configured on a respective support from the horizontal.

5. The patient support facility of claim 4, wherein each support of the at least two supports comprises two height adjustment facilities that together implement a tilting facility disposed in a transverse direction perpendicular to a longitudinal direction of the at least one patient support plate or the at least one patient support plate comprises at least one fastener for fastening at least one part of the patient.

6. The patient support facility of claim 4, wherein the height adjustment facility comprises at least one controllable actuator.

7. The patient support facility of claim 4, wherein the tilting facility comprises at least one controllable actuator controlled by the control facility.

8. The patient support facility of claim 1, wherein at least one setting data record includes at least one item of setting information for a height adjustment facility or a tilting facility.

9. The patient support facility of claim 1, wherein the control facility includes a storage device that is configured to store a database with setting data records, target data records, or setting data records and target data records that may be selected automatically or by a user.

10. An imaging facility comprising:
    a recording arrangement supported on a support facility; and
    a patient support facility comprising:
    at least one patient support plate;
    at least two supports for the at least one patient support plate, wherein each of the at least two supports are configured to be mobile and each comprise an autonomous drive module including a chassis that is configured to permit movements and rotations in all horizontal directions, a drive facility, and a control unit; and
    a control facility configured to operate the drive modules in a coordinated and individual manner;
    wherein the control facility is configured to consider a current posture of the recording arrangement relative to the at least two supports during actuation of the autonomous drive modules.

11. The imaging facility of claim 10, wherein the support facility further comprises an autonomous drive module with a chassis that is configured to permit p movements and rotations in all horizontal directions that is actuated by the control facility in a coordinated manner with the autonomous drive modules of the at least two supports.

12. The imaging facility of claim 10, wherein the patient support facility further comprises a first guidance facility, wherein the at least two supports include a second guidance facility, wherein the first and a respective second guidance facility are configured to engage with one another in order to arrange the at least one patient support plate in a detachable manner on at least one of the at least two supports.

13. The imaging facility of claim 10, wherein each of the at least two supports includes at least one height adjustment facility, at least one tilting facility for tilting the at least one patient support plate, or at least one height adjustment facility and at least one tilting facility for tilting the ate least one patient support plate configured on a respective support from the horizontal.

14. The imaging facility of claim 13, wherein each support of the at least two supports comprises two height adjustment facilities that together implement a tilting facility disposed in a transverse direction perpendicular to a longitudinal direction of the at least one patient support plate or the at least one patient support plate comprises at least one fastener for fastening at least one part of the patient.

15. The imaging facility of claim 13, wherein the height adjustment facility comprises at least one controllable actuator.

16. The imaging facility of claim 13, wherein the tilting facility comprises at least one controllable actuator controlled by the control facility.

17. The imaging facility of claim 10, wherein the control facility is configured to generate settings of a setting data record describing settings that contain an at least relative posture of the supports or is configured to autonomously assume an absolute target position or an absolute target position range of a target data record.

18. The imaging facility of claim 17, wherein the control facility includes a storage device that is configured to store a database with setting data records, target data records, or setting data records and target data records that may be selected automatically or by a user.

19. The imaging facility of claim 17, wherein at least one setting data record includes at least one item of setting information for a height adjustment facility or a tilting facility.

* * * * *